United States Patent

Papirov et al.

Patent Number: 6,146,322
Date of Patent: *Nov. 14, 2000

[54] IRRADIATING FILAMENT AND METHOD OF MAKING SAME

[75] Inventors: Igor I. Papirov; Anatolij I. Pikalov; Vladimir S. Shokurov; Sergej V. Sivtzov, all of Kharkov, Ukraine; Youri G. Popowski; Vitali E. Verin, both of Geneva, Switzerland

[73] Assignee: Schneider (Europe) AG, Bulach, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/739,649

[22] Filed: Oct. 30, 1996

[30] Foreign Application Priority Data

Dec. 5, 1995 [EP] European Pat. Off. ............. 95119124

[51] Int. Cl.[7] ...................................................... A61N 5/00
[52] U.S. Cl. ..................................................................... 600/3
[58] Field of Search ............................................. 600/1–8

[56] References Cited

U.S. PATENT DOCUMENTS

| 1,442,051 | 1/1923 | Cummings . | |
| 2,546,761 | 3/1951 | Loftus | 128/1.2 |
| 2,862,108 | 11/1958 | Meilink | 250/106 |

(List continued on next page.)

FOREIGN PATENT DOCUMENTS

| 2166915 | 8/1996 | Canada . |
| 0152124A3 | 8/1985 | European Pat. Off. . |

(List continued on next page.)

OTHER PUBLICATIONS

Search Report in corresponding European patent application EP 95119124.6, together with Communication and one-page Annex.

"Strontium–90—Applikator für interstitielle Bestrahlung der Hypophyse," Fortschritte auf dem Begiete der Röntgenstrahlen und den Nuklearmedizin, Holmer et al., pp. 574–578 (1967), with English translation.

(List continued on next page.)

*Primary Examiner*—John P. Lacyk
*Attorney, Agent, or Firm*—Crompton, Seager & Tufte, LLC

[57] ABSTRACT

A filament for irradiating a living body has a core material capable of irradiating radioactive radiation clad in a tubular casing of protective material different from the material forming the core. The materials forming the core and casing have a purity not less than 99.5 atomic percent and a grain size not exceeding 30 $\mu$m and the outer diameter of the filament is not less than 80 $\mu$m.

30 Claims, 2 Drawing Sheets

U.S. PATENT DOCUMENTS

| | | | |
|---|---|---|---|
| 2,955,208 | 10/1960 | Stevens | 250/108 |
| 3,060,924 | 10/1962 | Rush | 128/1.2 |
| 3,147,383 | 5/1962 | Prest | 250/108 |
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries, Jr. et al. | 250/108 R |
| 3,669,093 | 6/1972 | Sauerwein et al. | 128/1.1 |
| 3,674,006 | 7/1972 | Holmer | 128/1.2 |
| 3,750,653 | 8/1973 | Simon | 128/1.2 |
| 3,811,426 | 5/1974 | Culver et al. | 128/1.2 |
| 3,861,380 | 1/1972 | Chassagne et al. | 128/1.2 |
| 3,866,050 | 2/1975 | Whitfield | 250/497 |
| 3,927,325 | 12/1975 | Hungate et al. | 250/435 |
| 3,970,073 | 7/1976 | Greene | 128/1.2 |
| 4,096,862 | 6/1978 | DeLuca | 128/348 |
| 4,220,864 | 9/1980 | Sauerwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parsons, Jr. et al. | 250/497 |
| 4,314,157 | 2/1982 | Gaines | 250/497 |
| 4,364,376 | 12/1982 | Bigham | 128/1.1 |
| 4,402,308 | 9/1983 | Scott | 128/1.2 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,697,575 | 10/1987 | Horowitz | 128/1.2 |
| 4,702,228 | 10/1987 | Russell, Jr. et al. | 128/1.2 |
| 4,706,652 | 11/1987 | Horowitz | 128/1.2 |
| 4,763,642 | 8/1988 | Horowitz | 128/1.2 |
| 4,763,671 | 8/1988 | Goffinet | 128/786 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,881,938 | 11/1989 | van't Hooft | 600/3 |
| 4,897,076 | 1/1990 | Puthawala et al. | 600/7 |
| 4,936,823 | 6/1990 | Colvin et al. | 600/7 |
| 4,940,452 | 7/1990 | Rohe et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,994,013 | 2/1991 | Suthanthiran et al. | 600/8 |
| 5,030,194 | 7/1991 | Van't Hooft | 600/3 |
| 5,059,166 | 10/1991 | Fischell et al. | 600/3 |
| 5,069,226 | 12/1991 | Yamauchi et al. | 128/772 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,092,877 | 3/1992 | Pinchuk | 623/1 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/7 |
| 5,267,960 | 12/1993 | Hayman et al. | 604/106 |
| 5,282,781 | 2/1994 | Liprie | 600/3 |
| 5,302,168 | 4/1994 | Hess | 600/3 |
| 5,322,499 | 6/1994 | Liprie | 600/8 |
| 5,342,283 | 8/1994 | Good | 600/8 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,395,300 | 3/1995 | Liprie | 600/3 |
| 5,405,309 | 4/1995 | Carden, Jr. | 600/3 |
| 5,411,466 | 5/1995 | Hess | 600/3 |
| 5,425,720 | 6/1995 | Rogalsky et al. | 604/198 |
| 5,429,582 | 7/1995 | William | 600/2 |
| 5,460,592 | 10/1995 | Langton et al. | 600/7 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Tierstein | 604/104 |
| 5,556,389 | 9/1996 | Liprie | 604/264 |
| 5,575,749 | 11/1996 | Liprie | 600/3 |
| 5,605,530 | 2/1997 | Fischell et al. | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlien et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,713,828 | 2/1998 | Coniglione | 600/7 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,906,573 | 5/1999 | Aretz | 600/3 |
| 5,910,101 | 6/1999 | Andrews et al. | 600/3 |
| 5,910,102 | 6/1999 | Hastings | 600/3 |
| 5,913,813 | 6/1999 | Williams et al. | 600/3 |
| 5,916,143 | 6/1999 | Apple et al. | 600/3 |
| 5,919,126 | 7/1999 | Armini | 600/3 |
| 5,924,973 | 7/1999 | Weinberger | 600/3 |
| 5,924,974 | 7/1999 | Loffler | 600/3 |
| 5,938,582 | 8/1999 | Ciamacco, Jr. et al. | 600/3 |
| 5,947,889 | 9/1999 | Hehrlein | 600/3 |
| 5,947,924 | 9/1999 | Liprie | 604/96 |
| 5,947,958 | 9/1999 | Woodard et al. | 606/1.5 |
| 5,957,829 | 9/1999 | Thornton | 600/3 |
| 5,961,439 | 10/1999 | Chernomorsky et al. | 600/4 |
| 5,967,966 | 10/1999 | Kronholz et al. | 600/3 |
| 5,971,909 | 10/1999 | Bradshaw et al. | 600/3 |
| 5,976,106 | 11/1999 | Verin et al. | 604/96 |
| 5,997,462 | 12/1999 | Loffler | 600/3 |
| 5,997,463 | 12/1999 | Cutrer | 600/8 |
| 6,010,445 | 1/2000 | Armini et al. | 600/3 |
| 6,013,019 | 1/2000 | Fischell et al. | 600/3 |
| 6,013,020 | 1/2000 | Meloul et al. | 600/7 |
| 6,024,690 | 2/2000 | Lee et al. | 600/3 |
| 6,030,333 | 2/2000 | Sioshansi et al. | 600/3 |
| 6,033,357 | 3/2000 | Ciezki et al. | 600/3 |

FOREIGN PATENT DOCUMENTS

| | | |
|---|---|---|
| 0158630A3 | 10/1985 | European Pat. Off. . |
| 0308630A1 | 3/1989 | European Pat. Off. . |

| | | |
|---|---|---|
| 0 593 136 B1 | 12/1990 | European Pat. Off. . |
| 0433011A1 | 6/1991 | European Pat. Off. . |
| 0447745A2 | 9/1991 | European Pat. Off. . |
| 0466681A1 | 1/1992 | European Pat. Off. . |
| 0474994A1 | 3/1992 | European Pat. Off. . |
| 0 514 913 A2 | 5/1992 | European Pat. Off. . |
| 0 633 041 A1 | 7/1993 | European Pat. Off. . |
| 0 696 906 B1 | 4/1994 | European Pat. Off. . |
| 0 688 580 A1 | 6/1994 | European Pat. Off. . |
| 0621015A1 | 10/1994 | European Pat. Off. . |
| 0633041A1 | 1/1995 | European Pat. Off. . |
| 0668088A1 | 8/1995 | European Pat. Off. . |
| 0 686 342 | 12/1995 | European Pat. Off. . |
| 0 778 051 A1 | 12/1995 | European Pat. Off. . |
| 0686342A1 | 12/1995 | European Pat. Off. . |
| 0 754 473 A2 | 7/1996 | European Pat. Off. . |
| 0 754 472 A2 | 1/1997 | European Pat. Off. . |
| 0 801 961 A2 | 4/1997 | European Pat. Off. . |
| 0 810 004 | 12/1997 | European Pat. Off. . |
| 0 813 894 A2 | 12/1997 | European Pat. Off. . |
| 0 749 764 A1 | 6/1998 | European Pat. Off. . |
| 0 865 803 | 9/1998 | European Pat. Off. . |
| 0 904 798 | 3/1999 | European Pat. Off. . |
| 0 904 799 | 3/1999 | European Pat. Off. . |
| 3620123A1 | 12/1987 | Germany . |
| 09102312 | 8/1992 | Germany . |
| 19754870 | 1/1997 | Germany . |
| 197 58 234 | 7/1999 | Germany . |
| 198 07 727 | 7/1999 | Germany . |
| 198 25 563 | 12/1999 | Germany . |
| 198 25 999 | 12/1999 | Germany . |
| 198 26 000 | 12/1999 | Germany . |
| 198 29 447 | 1/2000 | Germany . |
| 10-071210 | 3/1998 | Japan . |
| 793158 | 4/1958 | United Kingdom . |
| WO 86/03124 | 6/1986 | WIPO . |
| 8903197 | 4/1989 | WIPO . |
| 9200776 | 1/1992 | WIPO . |
| 9203179 | 3/1992 | WIPO . |
| 9218051 | 10/1992 | WIPO . |
| 9304735 | 3/1993 | WIPO . |
| WO 93/04735 | 3/1993 | WIPO . |
| 9319803 | 10/1993 | WIPO . |
| 9319804 | 10/1993 | WIPO . |
| 9400847 | 1/1994 | WIPO . |
| 9416646 | 8/1994 | WIPO . |
| WO 94/25106 | 11/1994 | WIPO . |
| WO 94/26205 | 11/1994 | WIPO . |
| WO 95/07732 | 3/1995 | WIPO . |
| 9530384 | 11/1995 | WIPO . |
| 9606654 | 3/1996 | WIPO . |
| WO 96/10436 | 4/1996 | WIPO . |
| WO 96/13303 | 5/1996 | WIPO . |
| WO 96/14898 | 5/1996 | WIPO . |
| 9617654 | 6/1996 | WIPO . |
| WO 96/22121 | 7/1996 | WIPO . |
| WO 96/29943 | 10/1996 | WIPO . |
| WO 96/40352 | 12/1996 | WIPO . |
| WO 97/07740 | 3/1997 | WIPO . |
| WO 97/09937 | 3/1997 | WIPO . |
| WO 97/17029 | 5/1997 | WIPO . |
| WO 97/18012 | 5/1997 | WIPO . |
| WO 97/19706 | 6/1997 | WIPO . |
| WO 97/25102 | 7/1997 | WIPO . |
| WO 97/25103 | 7/1997 | WIPO . |
| WO 97/40889 | 11/1997 | WIPO . |
| WO 98/01183 | 1/1998 | WIPO . |
| WO 98/01184 | 1/1998 | WIPO . |
| WO 98/01185 | 1/1998 | WIPO . |
| WO 98/01186 | 1/1998 | WIPO . |
| WO 98/11936 | 3/1998 | WIPO . |
| WO 98/16151 | 4/1998 | WIPO . |
| WO 98/20935 | 5/1998 | WIPO . |
| WO 98/25674 | 6/1998 | WIPO . |
| WO 98/29049 | 7/1998 | WIPO . |
| WO 98/30273 | 7/1998 | WIPO . |
| WO 98/34681 | 8/1998 | WIPO . |
| WO 98/36769 | 8/1998 | WIPO . |
| WO 98/36788 | 8/1998 | WIPO . |
| WO 98/39052 | 9/1998 | WIPO . |
| WO 98/39062 | 9/1998 | WIPO . |
| WO 98/39063 | 9/1998 | WIPO . |
| WO 98/40032 | 9/1998 | WIPO . |
| WO 98/46309 | 10/1998 | WIPO . |
| WO 99/21615 | 5/1999 | WIPO . |
| WO 99/21616 | 5/1999 | WIPO . |
| WO 99/22774 | 5/1999 | WIPO . |
| WO 99/22775 | 5/1999 | WIPO . |
| WO 99/22812 | 5/1999 | WIPO . |
| WO 99/22815 | 5/1999 | WIPO . |
| WO 99/24116 | 5/1999 | WIPO . |
| WO 99/24117 | 5/1999 | WIPO . |
| WO 99/29354 | 6/1999 | WIPO . |
| WO 99/29370 | 6/1999 | WIPO . |
| WO 99/29371 | 6/1999 | WIPO . |
| WO 99/30779 | 6/1999 | WIPO . |
| WO 99/34969 | 7/1999 | WIPO . |
| WO 99/36121 | 7/1999 | WIPO . |
| WO 99/39628 | 8/1999 | WIPO . |
| WO 99/40962 | 8/1999 | WIPO . |
| WO 99/40970 | 8/1999 | WIPO . |
| WO 99/40971 | 8/1999 | WIPO . |
| WO 99/40972 | 8/1999 | WIPO . |
| WO 99/40973 | 8/1999 | WIPO . |
| WO 99/40974 | 8/1999 | WIPO . |
| WO 99/42162 | 8/1999 | WIPO . |
| WO 99/42163 | 8/1999 | WIPO . |
| WO 99/42177 | 8/1999 | WIPO . |
| WO 99/44686 | 9/1999 | WIPO . |
| WO 99/44687 | 9/1999 | WIPO . |
| WO 99/49935 | 10/1999 | WIPO . |
| WO 99/56825 | 11/1999 | WIPO . |
| WO 99/56828 | 11/1999 | WIPO . |
| WO 99-61107 | 12/1999 | WIPO . |
| WO 99/62598 | 12/1999 | WIPO . |
| WO 99/66979 | 12/1999 | WIPO . |
| WO 00/03292 | 1/2000 | WIPO . |
| WO 00/04838 | 2/2000 | WIPO . |
| WO 00/04953 | 2/2000 | WIPO . |
| WO 00/09212 | 2/2000 | WIPO . |

OTHER PUBLICATIONS

Introduction to Modern Physics, Richtmyer, Kennard, and Lauritsen, Fifth Edition, 1955.

The Atomic Nucleus, Robley D. Evans, Ph.D., Massachusetts Institute of Technology, pp. 608–629, 1955.

"Strengthening mechanisms in Elgiloy", Journal of Materials Science 19 (1984), pp. 2815–2836.

Fort Wayne Metals Brochure—Drawn Filled Tubing.

*Heat Treament, Structure and Properties of Nonferrous Alloys*, Charlie R. Brooks, American Society for Metals, Jul. 1990, pp. 33, 51, and 330–331.

*Mechanical Metallurgy*, George R. Dieter, McGraw–Hill, Inc., 1976, p. 560.

IRRADIATING FILAMENT AND METHOD OF MAKING SAME

BACKGROUND OF THE INVENTION

This invention relates to a filament for irradiating a living body, comprising a core of material capable of irradiating radioactive radiation after activation, the core being clad in a casing of protective material, wherein the materials forming the core and casing differ from one another.

The invention also relates to a method for producing a filament for irradiating a living body.

Endoluminal brachytherapy, and more particularly percutaneous transluminal brachytherapy, currently face difficulties for handling the radioactive material, either on a therapeutical viewpoint or on a manufacturing viewpoint. As a matter of fact, it is quite frequent that the structure embodying the radioactive material is bulky and lacks flexibility, whereby the material is difficult to operate through tortuous vessel configurations or narrow passages thereof; this may cause damage or even destruction of the radioactive structure together with the resulting risk of harmful influence on the organism. Furthermore, the radioactive material may enter into direct contact with the vessel walls, which greatly amplifies the risk of unwanted damage to the vessel. And when the radioactive material is merely coated or covered by an outer material, the coating or cover may help protecting the vessel wall from direct contact with the radioactive source, but there is still a substantial danger of having the radioactive material or particles thereof entering into unwanted contact with the vessel wall in case of deterioration of the coating or cover or because the coating or cover still have uncontrolled pores through which the radioactive material may cause damage to the vessel.

For example, the document WO 93/04735 describes an apparatus for the treatment of an artery, comprising a radioactive dose and means operatively connected to such a dose to bring it into a selected region of an artery. In one embodiment, the apparatus comprises a wire wound sheath removably positioned over a windowed housing made of a wire winding containing a radioactive dose, whereby relative motion between the sheath and housing permits moving the windowed housing in and out of the sheath to expose the radioactive dose in some place of an artery. In another embodiment the apparatus comprises a motion wire having a radioactive dose affixed at its distal end and a retractable sheath formed of a helically wound member positioned over the motion wire and radioactive configuration to provide a measure of shielding to the radioactive dose during insertion and removal of the system into an artery, whereby the sheath may be retracted to expose the radioactive dose at a selected place in the artery. A further embodiment comprises a shaft portion having at its distal end a canister containing a radioactive dose and provided with a remotely actuated window which can be manipulated to expose the radioactive dose in an injured area of an artery. In a still further embodiment, a plurality of radioactive dose means are encased in a heat shrinkable polymer catheter tip having spacers made of a meltable material to provide encapsulation of the radioactive dose means, which provides flexibility of the apparatus but not longitudinal homogeneity of the radioactive source. In a balloon configuration of the apparatus, radioactive elements are affixed to the outer surface of an angioplasty balloon. In a stent arrangement of the apparatus, the radioactive element may be associated with an expandable stent and it is the radioactive means that may be included in the stent as a cladding, a coating, or an additive within the basic stent material, or an attachment by other means to the stent.

As a further example of the aforesaid drawbacks, U.S. Pat. No. 5,059,166 describes an intra-arterial stent with the capability to inhibit intimal hyperplasia by means of radioactive radiation. The document refers to a radioisotope integral to an arterial stent which can irradiate the tissue in close proximity to the implantation site of the stent. In one embodiment, a helical coil spring stent is fabricated from a pure metal or alloy which has been activated so that it has become radioactive, i.e., it is a radioisotope; the radioisotope used for this purpose may be an alpha, beta, or gamma emitter, a beta emitter such as Vanadium 48 being preferred because of its short travel in human tissue and 16 days half-life and only 8% of emitted energy from gamma radiation. In another configuration, the stent spring wire is made from a metal such as steel into which is alloyed an element that can be made into a radioisotope, for example Phosphorus 32 which is a 14.3 day half-life beta emitter. In a further configuration, the stent wire is made from a radioisotope core material with an outer covering that has the attributes that are desirable for being a coil spring. In a variant, the stent wire is made of a radioisotope coating plated onto a spring material core. Still a further embodiment shows a more complex configuration in which a core of some material suited for stents is plated with a radioisotope coating which is in turn coated with an anti-thrombogenic coating such as carbon.

Within the frame of a centering configuration aimed at uniformly applying a radioactive radiation to a vessel wall, the document EP 0633041 A1 outlines the use of a radioactive emitter in the form of a filament of small diameter, which may be coiled. Filament technology has the advantage of a dense concentration of the radioactive dose in a small volume of the source allowing a reduced diameter and a better maneuverability in narrow and/or tortuous vessels. In one embodiment, the filament may be made of 89 Yttrium heat elaborated under vacuum to a diameter equal to or less than 0.2 mm.

In the environment of a medical appliance for the treatment of body vessels by ionizing radiation described in EP 0 686 342 A1, published Dec. 13, 1995, the filament technology is enhanced by having a filament, which may be in the form of a coil, coated by a neutral material such as Titanium.

Clad composite filaments are generally shown in WO 94/16646 and WO 95/30384.

All documents cited herein, including the foregoing, are incorporated herein by reference in their entireties for all purposes.

It is an object of this invention to improve the conditions of use in a patient as well as those of handling the sources used for irradiating a living body and more particularly those sources used for endoluminal or percutaneous transluminal brachytherapy. It is a further object of the invention to improve such conditions by means of a filament which is highly safe.

Still a further object of the invention is a method for manufacturing a filament for irradiating a living body which is fully controllable, devoid of hazardous technological operations with radioactive substances, and which results in a product which practically eliminates the risk of having radioactive core materials or particles thereof entering into unwanted contact with a living body.

SUMMARY OF THE INVENTION

Accordingly, with the materials forming the core and protective casing having a grain size equal to or less than 30

μm, a filament is achieved which has all the advantages of the filament technology for dense concentration of radioactive dose and for exceptional flexibility and maneuverability through narrow and/or tortuous areas of body vessels. And this is achieved within a configuration in which the core and casing have a great homogeneity which strongly reduces brittleness of the materials and which practically eliminates any risk of having cracks or ruptures in case of deformation as well as any risk of having radioactive particles wandering through uncontrolled pores of the protective casing. Safe handling of the radioactive core is thus highly effective and there is no danger of unwanted harmful influence of the radioactive material on the organism.

Where the materials forming the core and protective casing have a grain size equal to or less than 10 μm, the filament achieves a further degree in terms of isotropic lateral flexibility and homogeneous distribution of the core material throughout the length of the filament, with a further safety in terms of brittleness reduction of the materials.

Where the materials forming the core and protective casing have a purity of at least 99.5 atomic percent, homogeneity of the filament is still enhanced with the corresponding safety and absence of brittleness. And when the material forming the core is alloyed by 0.1 to 0.3 atomic percent with the material forming the protective casing and the material forming the protective casing is alloyed by 0.1 to 0.3 atomic percent with the material forming the core, the strength of the filament is still strongly increased without any loss on the control of the tightness of the materials; the probability of cracks or damage to the assembly is further reduced. With a filament having an outer diameter equal to or over 80 μm a limit is achieved on the strength of the materials while retaining the aforesaid qualities; a filament of that size is specifically suitable for percutaneous transluminal procedures. With the materials forming the core and protective casing having the same crystal lattice, which may be advantageously a hexagonal crystal lattice, high purity and small grain size as well as the mechanical properties and pore control of the assembly are further enhanced.

Preferably, the material forming the core is a beta radiation emitter, and more particularly Yttrium or Thulium, to take advantage of an appreciable irradiation combined to a suitable half-life. This is desirable to allow procedure times that are manageable in interventional medicine such as percutaneous transluminal angioplasty. Moreover, beta emitters such as Yttrium or Thulium have a hexagonal crystal lattice which best fits to the employed casing material. Still preferably, the material forming the protective casing is Titanium, which has a short half-life and which is biocompatible while having very good mechanical properties providing absence of leakage of the core material. Moreover, the hexagonal crystal lattice of Titanium provides compatible deformation properties with the core materials.

The filament may be easily coiled to still further promote the elasticity of the resulting source in case of handling through tortuous vessels without the risk of damage or cracks in the assembly.

By the steps of forming an initial billet of core material capable to irradiate radioactive radiation after activation, forming an initial tubular preform of casing material differing from the core material, working the initial billet and tubular preform until they have a grain size equal to or less than 30 μm, inserting the billet into the tubular preform to have an assembly, drawing the assembly through a series of successive dies of decreasing size with intermediate annealing of the assembly in intervals between successive dies until the assembly has a final outer diameter, and end sealing of the casing material on the core material, a method for producing a filament is achieved which is fully controllable, allowing decrease of the internal stress and grain size of both the core and casing materials. Each draw sequence through a die reduces the grain size by fragmentation of the grains and the further re-crystallization occurring during the intermediate annealing between successive dies starts a re-crystallization at the reduced grain size. Growth of the grain is thus avoided; a 10 μm grain size may be securely achieved and from that basis it is readily possible to obtain a 5 to 7 μm grain size without any risk of uncontrolled growth of the grain size. Final sealing of the casing material on the core material may be made without affecting the structure of the materials. The resulting filament has thus a high homogeneity which reduces its brittleness and avoids the risk of having cracks or ruptures therein under current deformation. The risk of having unwanted radioactive particles wandering through uncontrolled pores of the filament is practically eliminated.

By the aforesaid method, the assembly comprising casing and core materials may be drawn up to an outer diameter equal to or over 80 μm without affecting the strength of the materials and qualities of the filament. And the method may comprise the step of coiling the drawn assembly before end sealing of the casing material on the core material, still without affecting their homogeneity and without any risk of cracks or ruptures in the filament.

When the method includes the step of cutting the drawn assembly into a plurality of sub-assemblies before end sealing of the casing material on the core material, whereas end sealing of the casing material on the core material is made on each of the sub-assemblies, filament assemblies may be produced economically in a continuous manner, the assemblies being then cut at will.

Advantageously, end sealing of the casing material on the core material is made by laser welding for a precise procedure.

When the core material and the protective casing material have a purity of at least 99.5 atomic percent, the method still achieves a greater homogeneity for the resulting filament under the same basics of fully controlled manufacture. And to enhance the mechanical properties of the filament while further reducing the probability of cracks or damage, the method may comprise the preliminary step of alloying the core material by 0.1 to 0.3 atomic percent with the casing material and alloying the casing material by 0.1 to 0.3 atomic percent with the core material.

To further enhance the technological feasibility of the process the core material and casing material may have the same crystal lattice, preferably a hexagonal crystal lattice which will fit best with compatible strength, plasticity and annealing temperatures.

When the method further comprises the step of activating the core material in the casing material in a nuclear reactor, activation is made at the final stage of production of the filament, which is easier and substantially reduces the manipulations of radioactive filament. The resulting cost is lower and the risks of contamination are strongly limited.

In sum, the present invention relates to a filament having a core of material capable of irradiating radioactive radiation after activation. The core is clad in a casing of protective material and the materials forming the core and casing differ from one another and have a grain size equal to or less than 30 μm. The filament materials forming the core and protective casing may have a grain size equal to or less than 10 μm.

The core and protective casing may have a purity of at least 99.5 atomic percent. The core may be alloyed by 0.1 to 0.3 atomic percent with the material forming the protective casing, and the material forming the protective casing may be alloyed by 0.1 to 0.3 atomic percent with the material forming the core. The filament may have an outer diameter equal to or over 80 µm. Also, the filament may form a coil. The core and protective casing may have the same crystal lattice, a hexagonal crystal lattice, or a cubic crystal lattice. The core may be a beta radiation emitter. The material forming the core may be Yttrium, Thulium, Europium, Gadolinium, Terbium, Iridium, or Cesium. The material forming the protective casing may be Titanium, Platinum, Silver, or Gold.

A first material may be adapted to emit radiation and a second material may cover the first material and the first and second material each may have a grain size equal to or less than about 30 µm.

The invention also relates to a method for producing a filament which includes forming an initial billet of core material capable of irradiating radioactive radiation after activation, forming an initial tubular preform of casing material differing from the core material, working the initial billet and tubular preform until they have a grain size equal to or less than 30 µm, inserting the billet into the tubular preform to form an assembly, drawing the assembly through a series of successive dies of decreasing size with intermediate annealing of the assembly and intervals between successive dies until the assembly has a final outer diameter, and sealing the casing material on the core material. The method may include a step where: the final outer diameter is equal to or over 80 µm; the drawn assembly is coiled before end sealing of the casing material on the core material; the drawn assembly is cut into a plurality of sub-assemblies before end sealing of the casing material on the core material, and end sealing of the casing material on the core material is made on each of the sub-assemblies; end sealing of the casing material on the core material is made by spot laser welding; the core material and the protective casing material have a purity of at least 99.5 atomic percent; the core material is alloyed by 0.1 to 0.3 atomic percent with the casing material and the casing material is alloyed by 0.1 to 0.3 atomic percent with the core material; the core material and the casing material have the same crystal lattice or a hexagonal crystal lattice; the core material is a beta radiation emitter; the core material is Yttrium or Thulium; the casing material is Titanium; activation of the core material in the casing material is in a nuclear reactor.

Another method for producing an irradiating filament includes providing a first material that emits radiation and providing a second material, working the first and second materials until each respective material has a grain size equal to or less than about 30 µm, disposing the first material within the second material to form a composite assembly having a first end and a second end, and drawing the composite assembly through a series of successively smaller dies and annealing the composite assembly. The method may include steps of covering and sealing the first end and second end with the second material.

These and other objects and features of the invention will become readily apparent from the following detailed description with reference to the accompanying drawings which illustrate, diagrammatically and by way of example only, two embodiments of a filament according to the invention.

DETAILED DESCRIPTION

Figure 1:
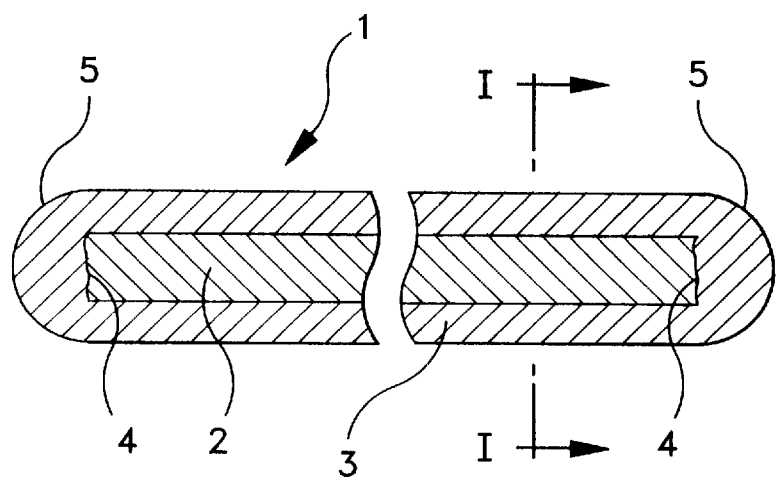
FIG. 1 is an axial cut of a filament according to the first embodiment.

The filament 1 shown in FIG. 1 comprises a core 2 of material capable of irradiating radioactive radiation. Preferably, the core 2 is made of a cylindrical wire of a beta radiation emitter such as Yttrium or Thulium having a purity of 99.5 atomic percent. Yttrium and Thulium both have a hexagonal crystal lattice and a relatively small grain size.

The core 2 is clad in a tubular casing 3 of protective material different from the material of the core 2. Preferably, the casing 3 is made of Titanium having a purity of 99.5 atomic percent, preferably 99.9 atomic percent. Titanium also has a hexagonal crystal lattice with a relatively small grain size.

The materials, Yttrium and Thulium, forming the core 2, and Titanium, forming the protective casing 3, have a grain size not exceeding 30 µm, preferably equal to or less than 10 µm. The outer diameter D of the filament 1 is not less than 80 µm.

Advantageously, the production of the filament 1 may be obtained by forming an initial billet of core material and an initial tubular preform of casing material differing from the core material. Such billet and tubular preform are worked, for instance by deformation and thermal treatment or as ingots and serial consequent hot drawing, until they have a grain size equal to or less than 30 µm. The billet is then inserted into the tubular preform to form an assembly which is drawn through a series of successive dies of decreasing size. In intervals between successive dies, the drawn assembly is allowed to anneal, which process provides a decrease in internal stress and allows formation of a small grain structure of the core and casing materials less than 30 µm. The casing is then hermetically sealed on the core 2, preferably by taking off by etching a portion of the Yttrium or Thulium wire at its ends 4, and thereafter closing the ends 5 of the Titanium tube 3 into a smooth spherical tip which does not substantially exceed the outer surface at the filament 1. For example, this procedure may be achieved by means of spot laser welding. After completion of this assembly, the filament may be brought into a nuclear reactor (not shown) for activation of the core 2 in the casing 3.

According to a variant, the material forming the core 2 may be alloyed by 0.1 to 0.3 atomic percent of the material forming the casing 3 with the material forming the casing 3 alloyed by 0.1 to 0.3 atomic percent of the material forming the core 2. The manufacturing process follows then as described hereabove.

Figure 3:
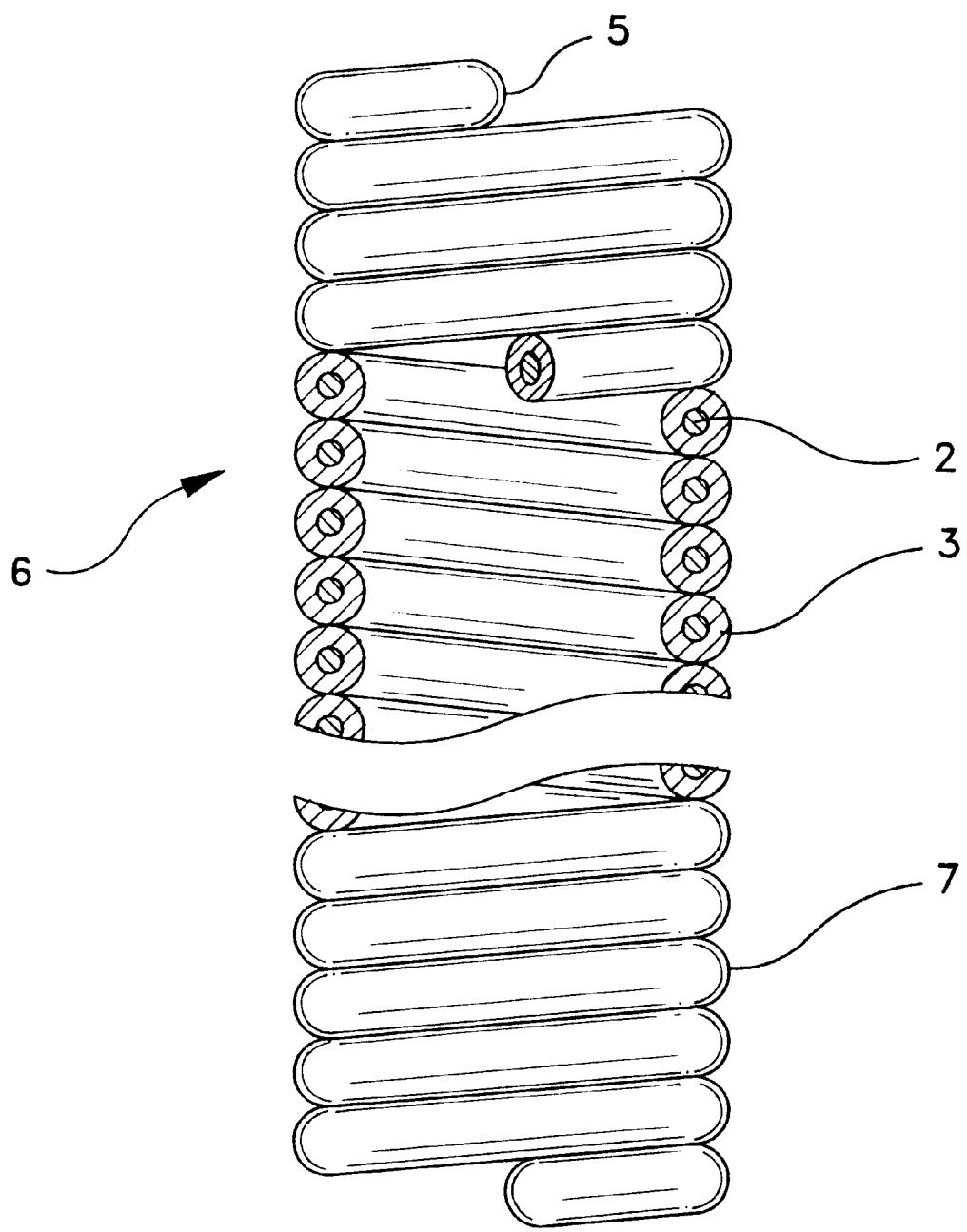
FIG. 3 is an axial view, partly cut, of a radiation source formed of a coiled filament according to the second embodiment.

The filament 6 shown in FIG. 3 is made identically as and with the same integers (bearing the same reference numerals) as the filament 1 of FIG. 1 or its alloyed variant. After completion of the assembly of core 2 and casing 3, the filament 6 is applied on a mandrel (not shown) in order to be formed as a coil 7 and then end sealing of the casing material on the core material is made as described hereabove. After completion of the assembly forming the filament 6 and its coil shaping 7 and sealing, the filament may be brought into a nuclear reactor for activation of the core 2 in the casing 3.

Variants are available. For instance, instead of Yttrium or Thulium, other emitters may be used for the core, more particularly Europium or Gadolinium or Terbium which also have a hexagonal crystal lattice. It is also possible to use other metals such as Platinum or Gold or Silver instead of Titanium for forming the casing 3, although such metals have a cubical crystal lattice. Such potential coverage materials could be preferably used with Iridium, Cesium or other core materials having a cubic crystal lattice.

Figure 2:
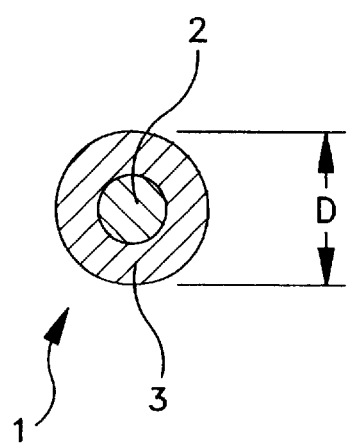
FIG. 2 is a cross section according to line I—I of FIG. 1.

The filament 1 as shown in FIGS. 1 and 2 may be used as such or affixed at the end of a guiding structure or of a guide wire as used in endoluminal or transluminal brachytherapy, or as a wire to partly or completely form or make part of a stent, in which case energization in the nuclear reactor will be made after completion of the stent structure.

It will be evident from considerations of the foregoing that the irradiating filament is now available and may be constructed using a number of methods, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

We claim:

1. A filament for irradiating a living body, comprising a core of radiation emitting material, the core being clad in a casing of protective material, wherein the materials forming the core and casing differ from one another and the materials forming the core and protective casing have a grain size equal to or less than 30 µm.

2. A filament according to claim 1, wherein the materials forming the core and protective casing have a grain size equal to or less than 10 µm.

3. A filament according to claim 1, wherein the materials forming the core and protective casing have a purity of at least 99.5 atomic percent.

4. A filament according to claim 1, wherein the material forming the core is alloyed by 0.1 to 0.3 atomic percent with the material forming the protective casing, and the material forming the protective casing is alloyed by 0.1 to 0.3 atomic percent with the material forming the core.

5. A filament according to claim 1, wherein the casing material has an outer diameter equal to or over 80 µm.

6. A filament according to claim 1, wherein the materials forming the core and protective casing have the same crystal lattice.

7. A filament according to claim 1, wherein the materials forming the core and protective casing have a hexagonal crystal lattice.

8. A filament according to claim 1, wherein the material forming the core and protective casing have a cubic crystal lattice.

9. A filament according to claim 1, wherein the filament forms a coil.

10. A filament according to claim 1, wherein the material forming the core is a beta radiation emitter.

11. A filament according to claim 1, wherein the material forming the protective casing is selected from the group consisting of Titanium, Platinum, Silver, and Gold.

12. A filament according to claim 1, wherein the material forming the core is selected from the group consisting of Yttrium, Thulium, Europium, Gadolinium, Terbium, Iridium, and Cesium.

13. A filament according to claim 12, wherein the material forming the core is Yttrium.

14. A filament according to claim 12, wherein the material forming the core is Thulium.

15. A filament according to claim 11, wherein the material forming the protective casing is Titanium.

16. An irradiating filament comprising:
a first material adapted to emit radiation and a second material covering the first material wherein the first and second material each have a grain size equal to or less than about 30 µm.

17. A clad composite filament comprising a core and a case, the core comprising a radiation emitting material and the case comprising a biocompatible material which is different than the radiation emitting material, wherein both of the radiation emitting material and the biocompatible material have a grain size which is less than or equal to 30 µm.

18. The filament of claim 17, wherein both of the radiation emitting material and the biocompatible material have a grain size which is less than or equal to 10 µm.

19. The filament of claim 17, wherein the radiation emitting material is alloyed with 0.1 to 0.3 atomic percent of the biocompatible material, and the biocompatible material is alloyed with 0.1 to 0.3 atomic percent of the radiation emitting material.

20. The filament of claim 17, wherein the case has an outer diameter of at least 80 µm.

21. The filament of claim 17, wherein the radiation emitting material and the biocompatible material have the same crystal lattice.

22. The filament of claim 17, wherein the radiation emitting material and the biocompatible material have hexagonal crystal lattices.

23. The filament of claim 17, wherein the radiaton emitting material and the biocompatible material have cubic crystal lattices.

24. The filament of claim 17, wherein the filament forms a coil.

25. The filament of claim 17, wherein the radiation emitting material is a beta radiation emitter.

26. The filament of claim 17, wherein the biocompatible material is selected from the group consisting of titanium, platinum, silver, gold, and alloys thereof.

27. The filament of claim 17, wherein the radiation emitting material is selected from the group consisting of yttrium, thulium, europium, gadolinium, terbium, iridium, cesium, and alloys thereof.

28. The filament of claim 27, wherein the radiation emitting material is yttrium.

29. The filament of claim 27, wherein the radiation emitting material is thulium.

30. The filament of claim 26, wherein the biocompatible material is titanium.

* * * * *